(12) United States Patent
Park et al.

(10) Patent No.: US 11,889,997 B2
(45) Date of Patent: Feb. 6, 2024

(54) BIOPSY INSTRUMENT HAVING OUTER NEEDLE-LOCKING MEMBER

(71) Applicant: GREEN MEDICAL SUPPLY., LTD, Hwaseong-si (KR)

(72) Inventors: Byeong Jun Park, Goyang-si (KR); Kyoung Eui Song, Hwaseong-si (KR)

(73) Assignee: GREEN MEDICAL SUPPLY., LTD, Hwaseong-si (KR)

( * ) Notice: Subject to any disclaimer, the term of this patent is extended or adjusted under 35 U.S.C. 154(b) by 534 days.

(21) Appl. No.: 17/281,677

(22) PCT Filed: Dec. 30, 2020

(86) PCT No.: PCT/KR2020/019424
§ 371 (c)(1),
(2) Date: Mar. 31, 2021

(87) PCT Pub. No.: WO2022/114381
PCT Pub. Date: Jun. 2, 2022

(65) Prior Publication Data
US 2022/0395264 A1    Dec. 15, 2022

(30) Foreign Application Priority Data
Nov. 26, 2020 (KR) .......... 10-2020-0161268

(51) Int. Cl.
*A61B 10/02* (2006.01)
(52) U.S. Cl.
CPC .. *A61B 10/0266* (2013.01); *A61B 2010/0208* (2013.01)

(58) Field of Classification Search
CPC ............ A61B 10/0233; A61B 10/0266; A61B 10/0275; A61B 2010/0208
See application file for complete search history.

(56) References Cited

FOREIGN PATENT DOCUMENTS

| | | | | |
|---|---|---|---|---|
| CN | 109106404 A | * | 1/2019 | ......... A61B 10/0266 |
| EP | 2 862 520 A1 | | 4/2015 | |
| JP | 4343309 B2 | | 10/2009 | |
| KR | 10-1168368 B1 | | 8/2012 | |
| KR | 10-2013-0079788 A | | 7/2013 | |
| KR | 10-2014-0106062 A | | 9/2014 | |
| KR | 10-1463867 B1 | | 12/2014 | |
| KR | 10-2015-0087230 A | | 7/2015 | |
| KR | 10-1551311 B1 | | 9/2015 | |
| KR | 10-1782765 B1 | | 9/2017 | |
| KR | 10-2020-0028166 A | | 3/2020 | |
| KR | 10-2020-0102039 A | | 8/2020 | |
| WO | 2018/213611 A1 | | 11/2018 | |

OTHER PUBLICATIONS

International Search Report dated Aug. 13, 2021 in Application No. PCT/KR2020/019424.

* cited by examiner

*Primary Examiner* — Eric F Winakur
*Assistant Examiner* — Abel Seifu Abegaz
(74) *Attorney, Agent, or Firm* — Sughrue Mion, PLLC

(57) ABSTRACT

Provided is a biopsy instrument having an outer needle-locking member, which is capable of checking whether an inner needle is placed in target tissue and shooting an outer needle after the tissue is sufficiently introduced into the inner needle, thereby accurately collecting the target tissue that is to be.

3 Claims, 12 Drawing Sheets

[Fig. 1]
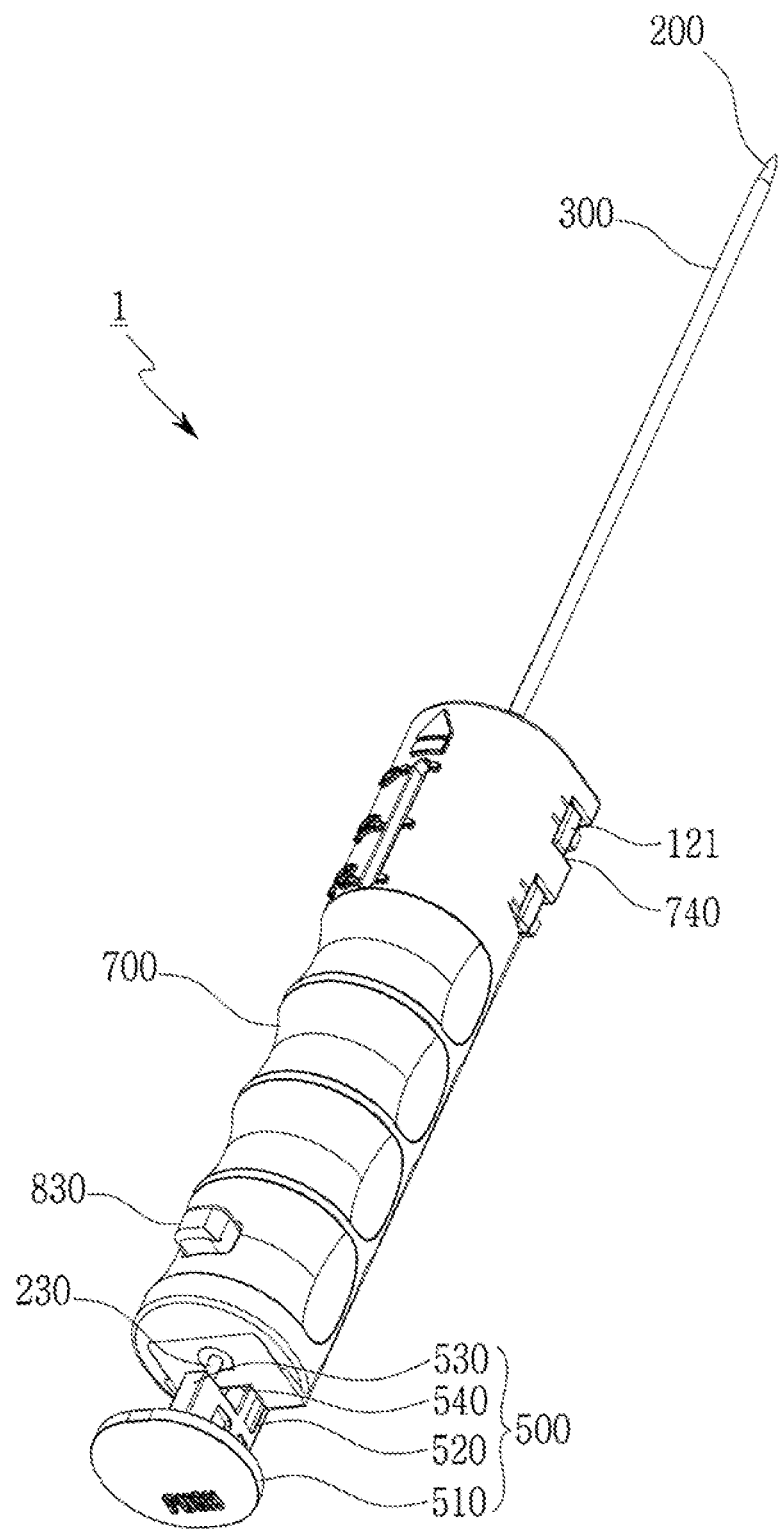

[Fig. 2]
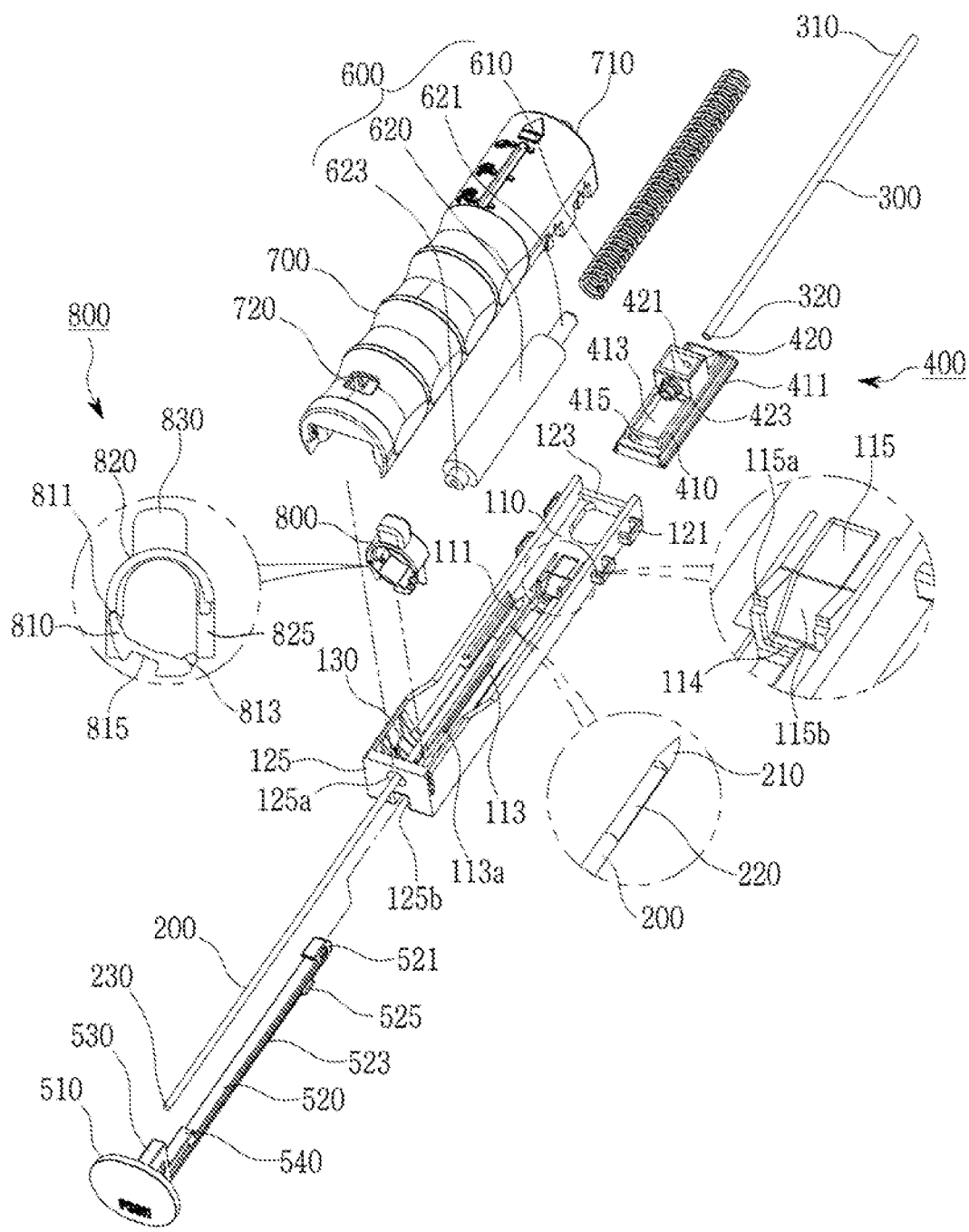

[Fig. 3]
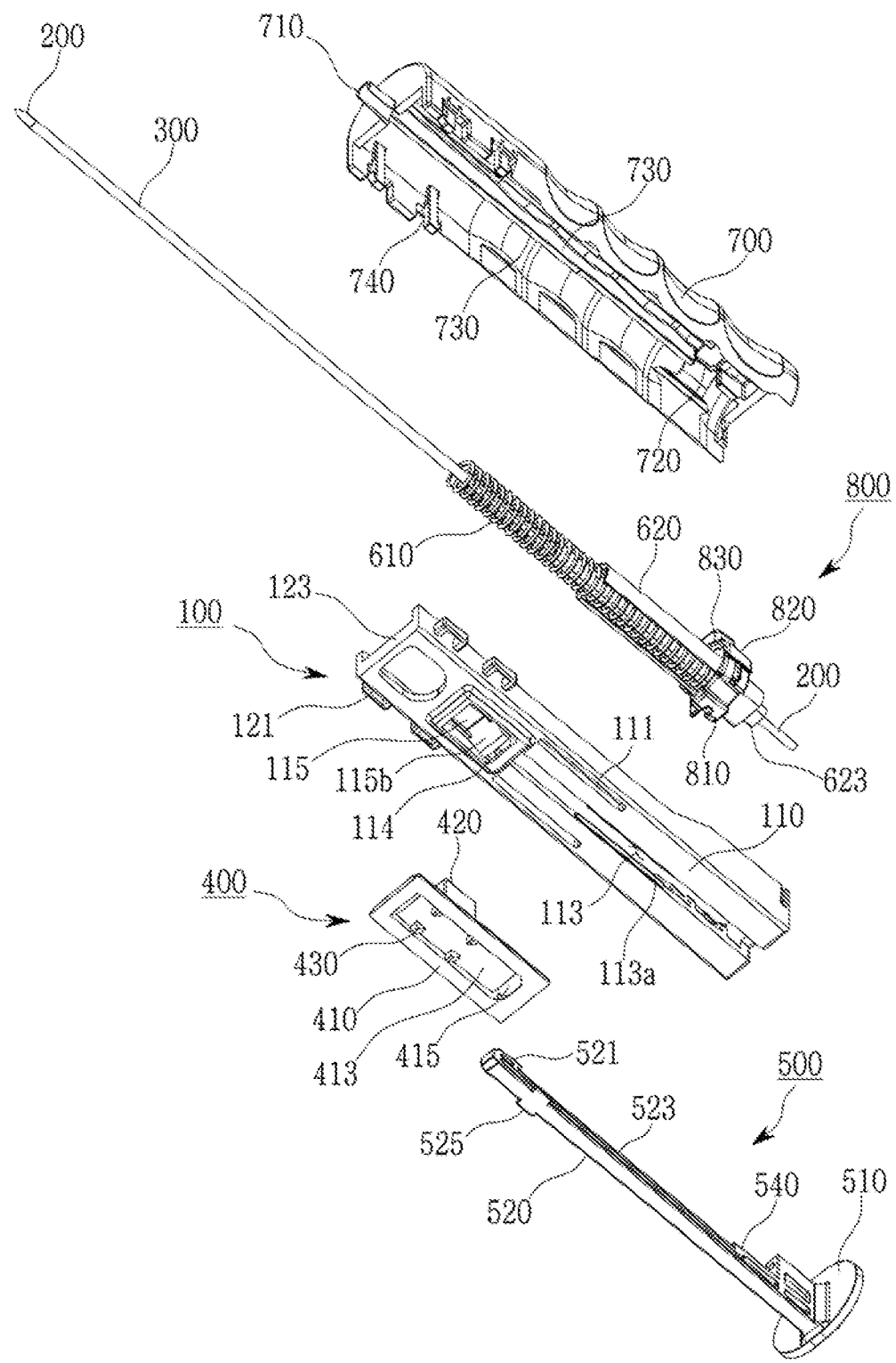

[Fig. 4]
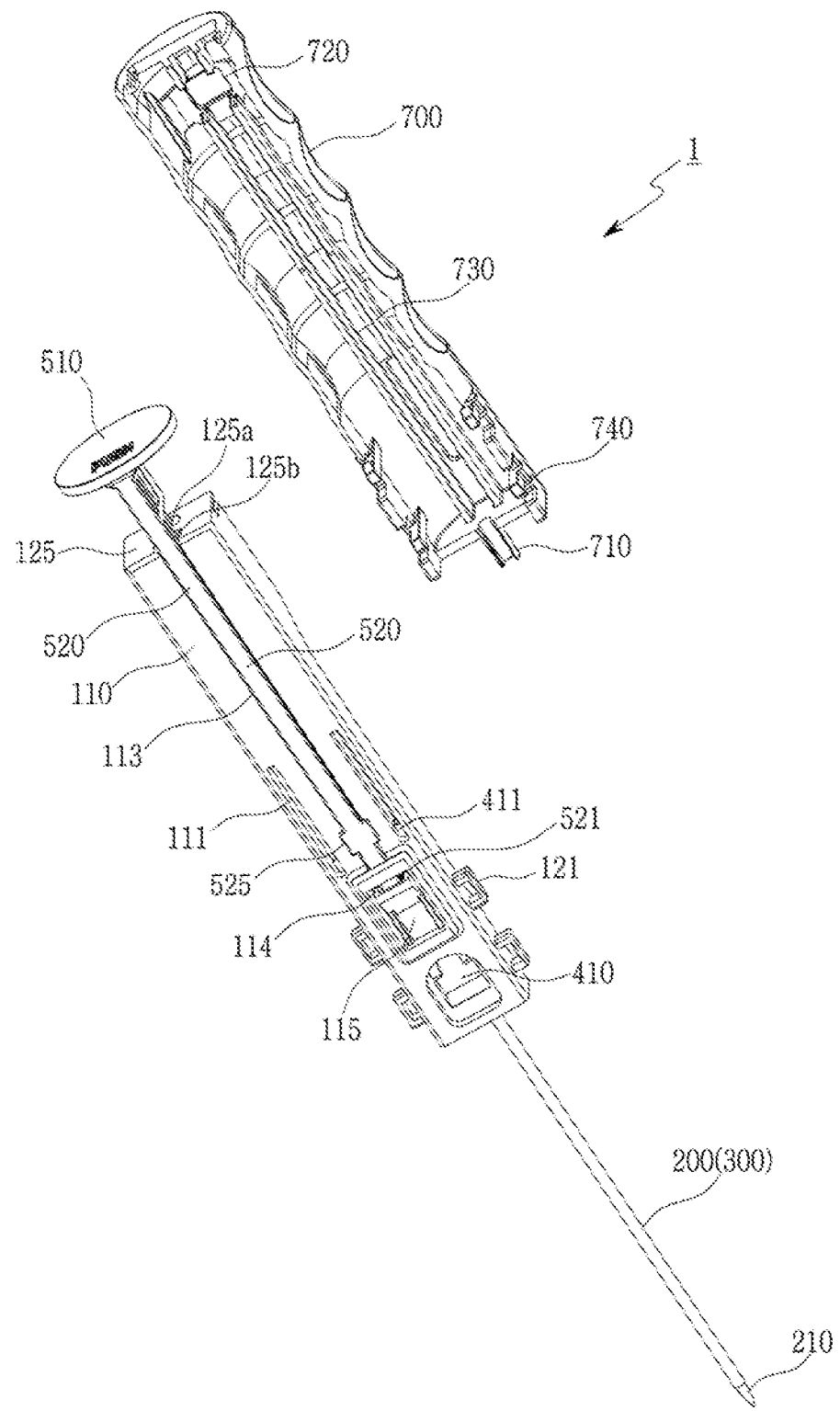

[Fig. 5]
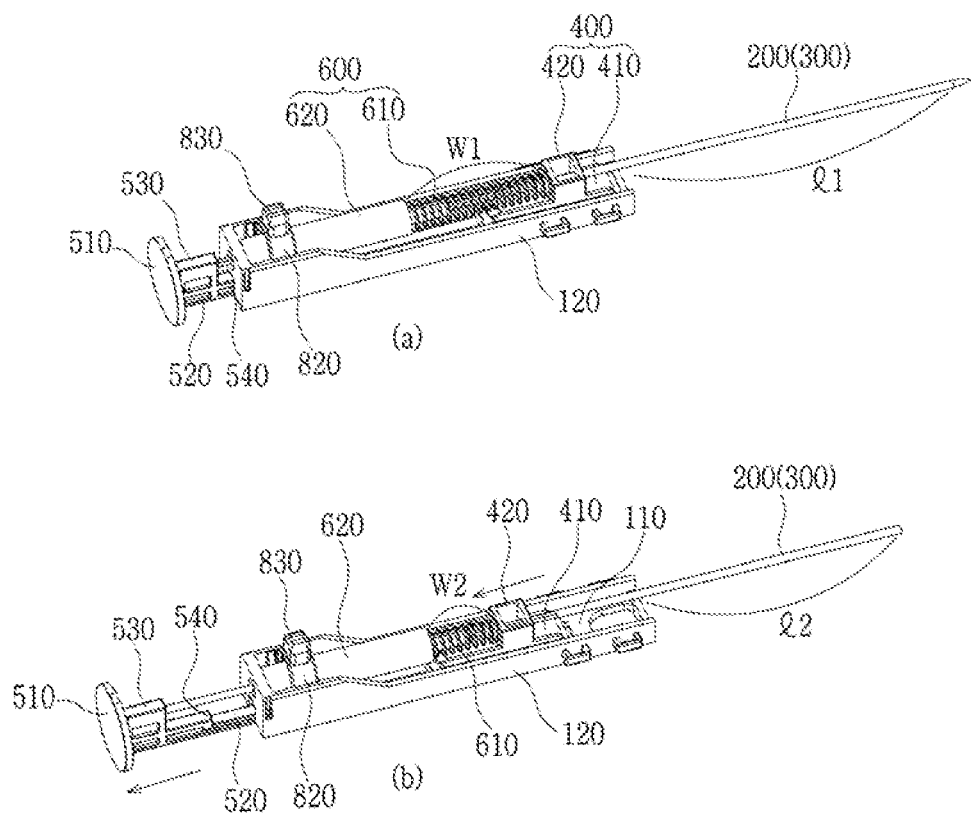

[Fig. 6]
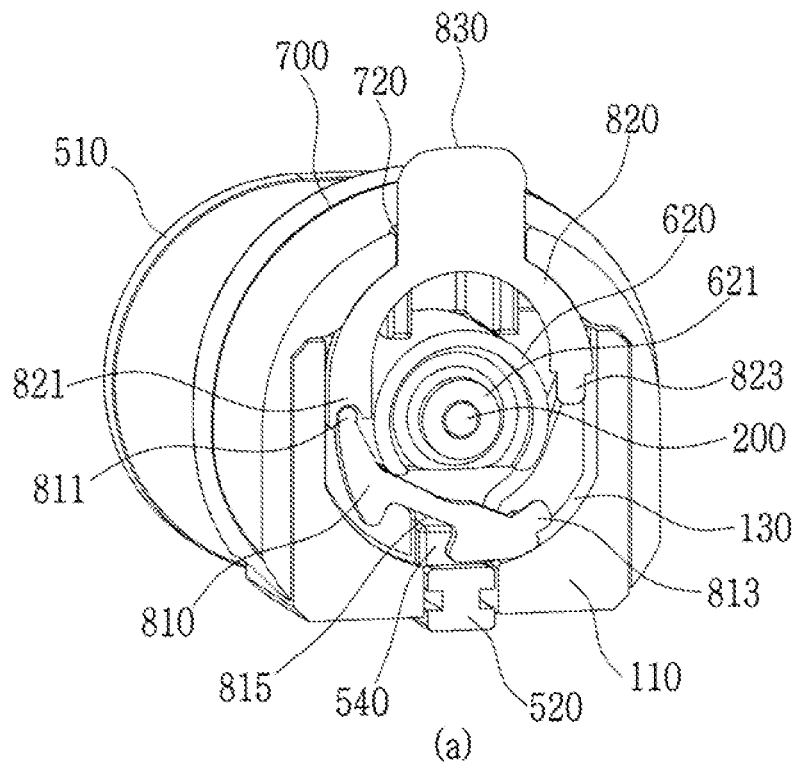
(a)
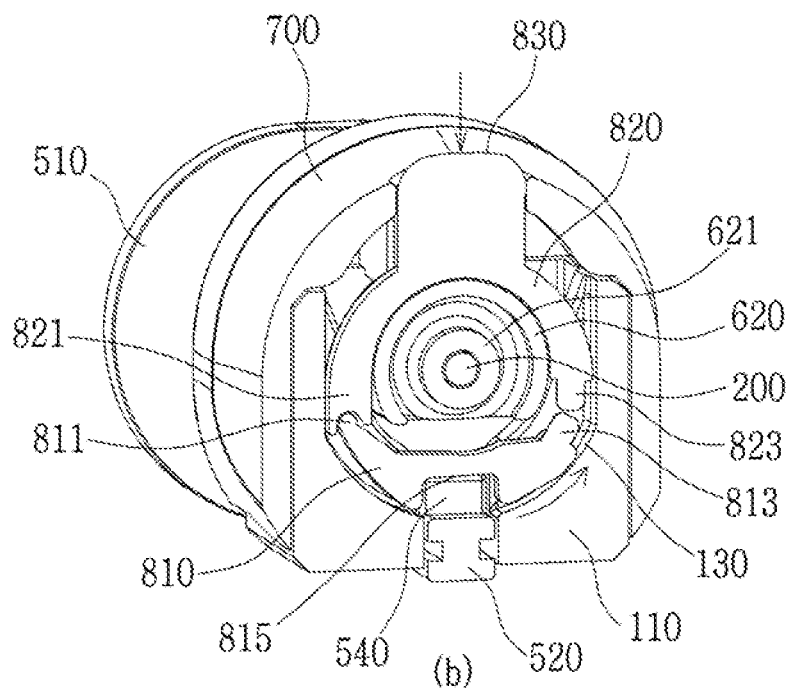
(b)

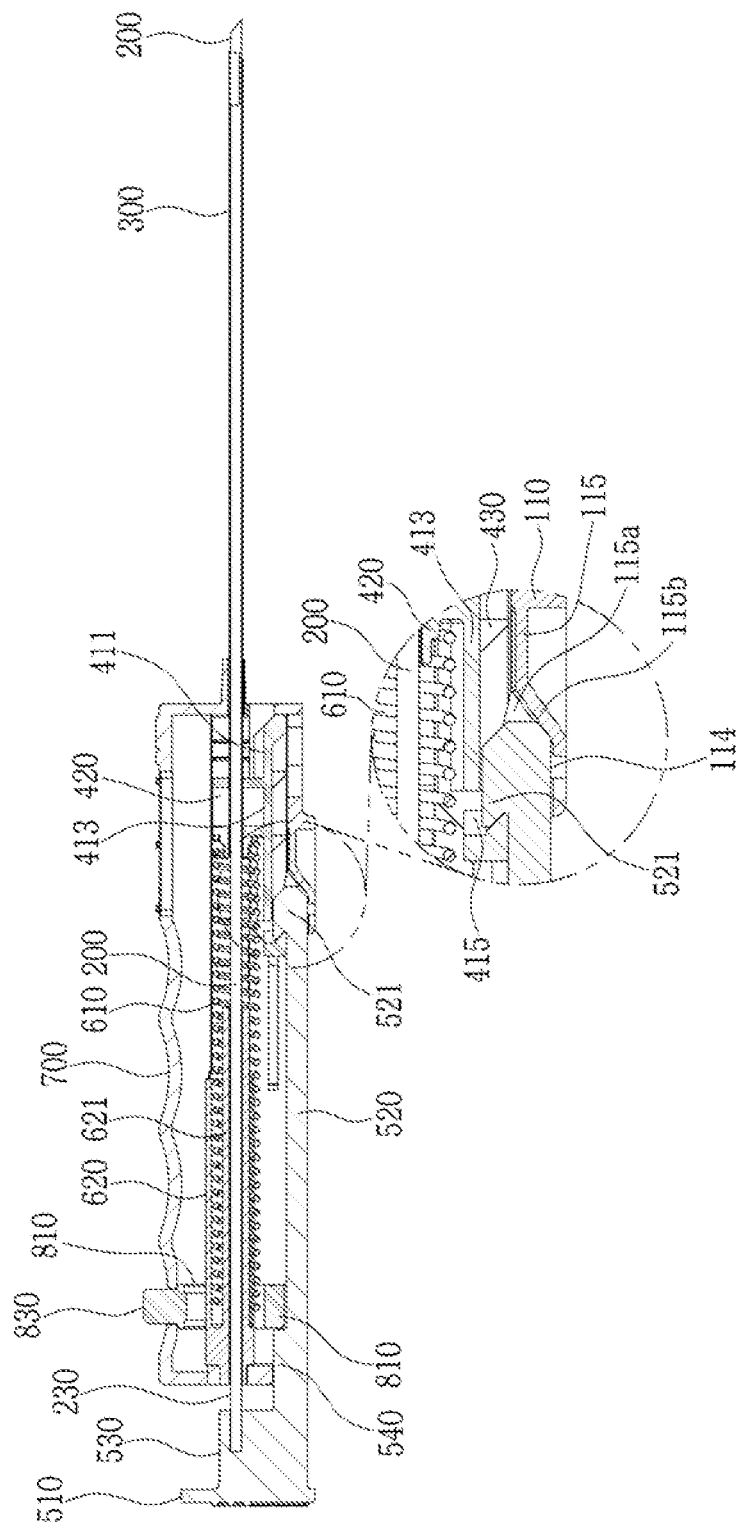
[Fig. 7]

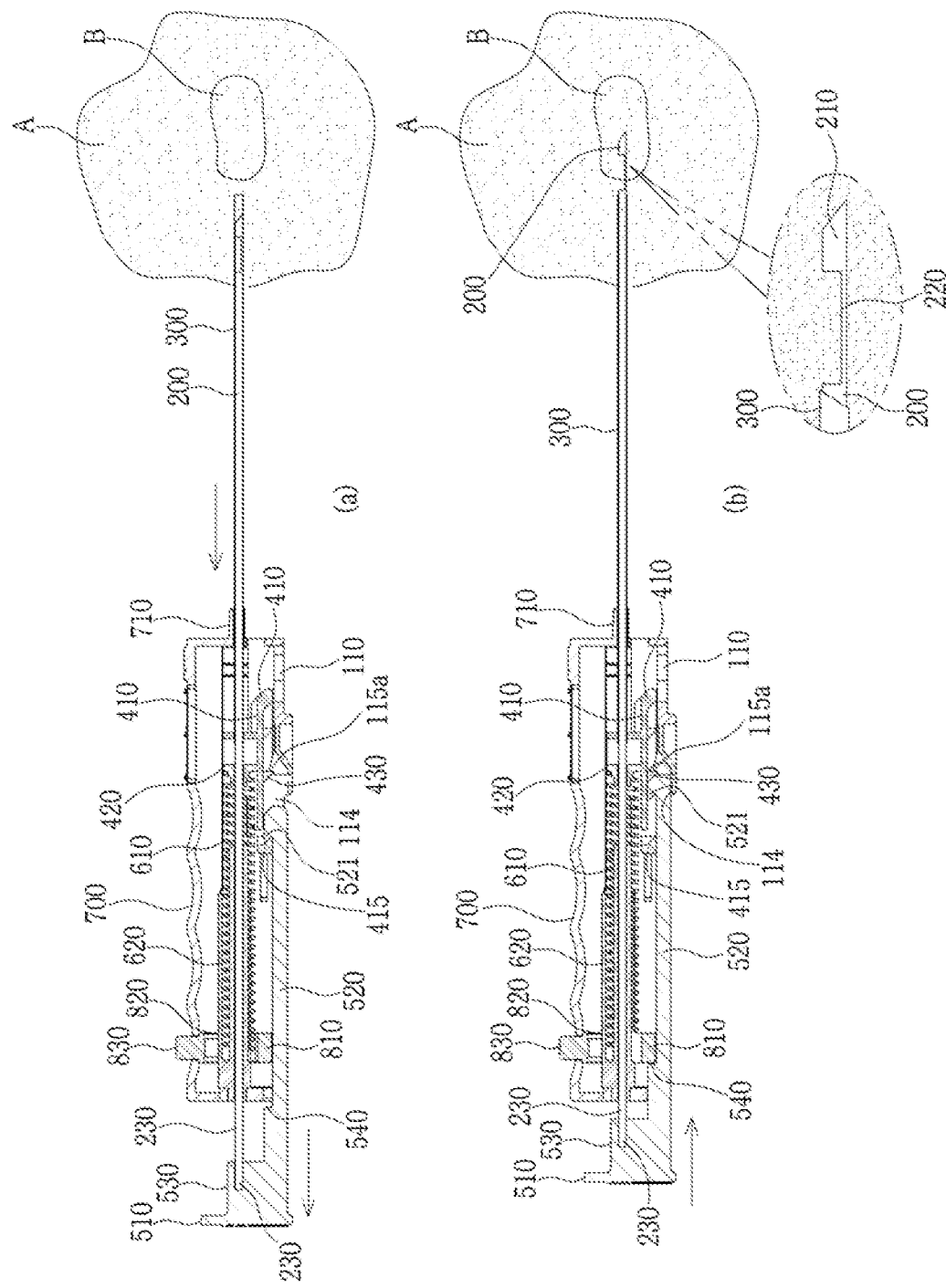
[Fig. 8]

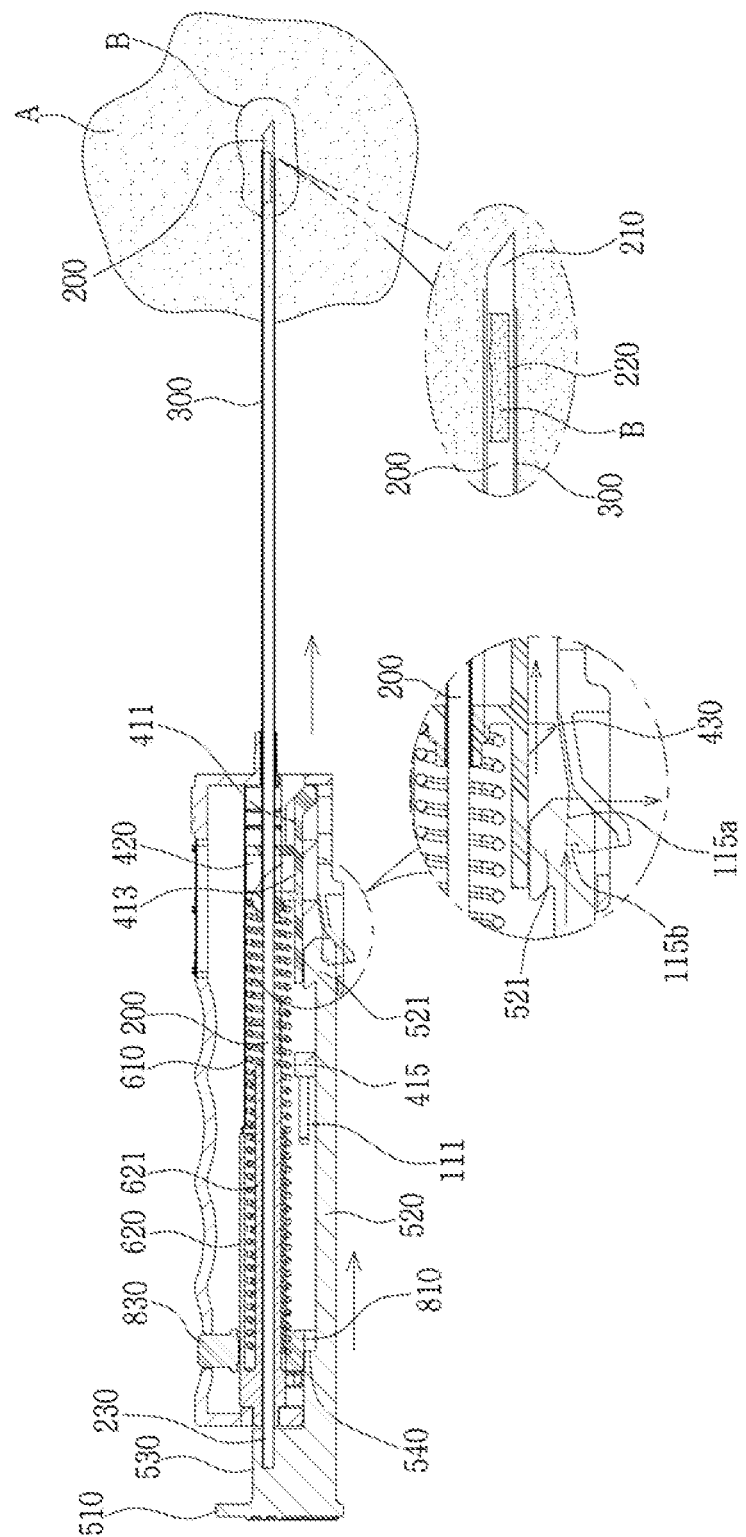
[Fig. 9]

[Fig. 10]
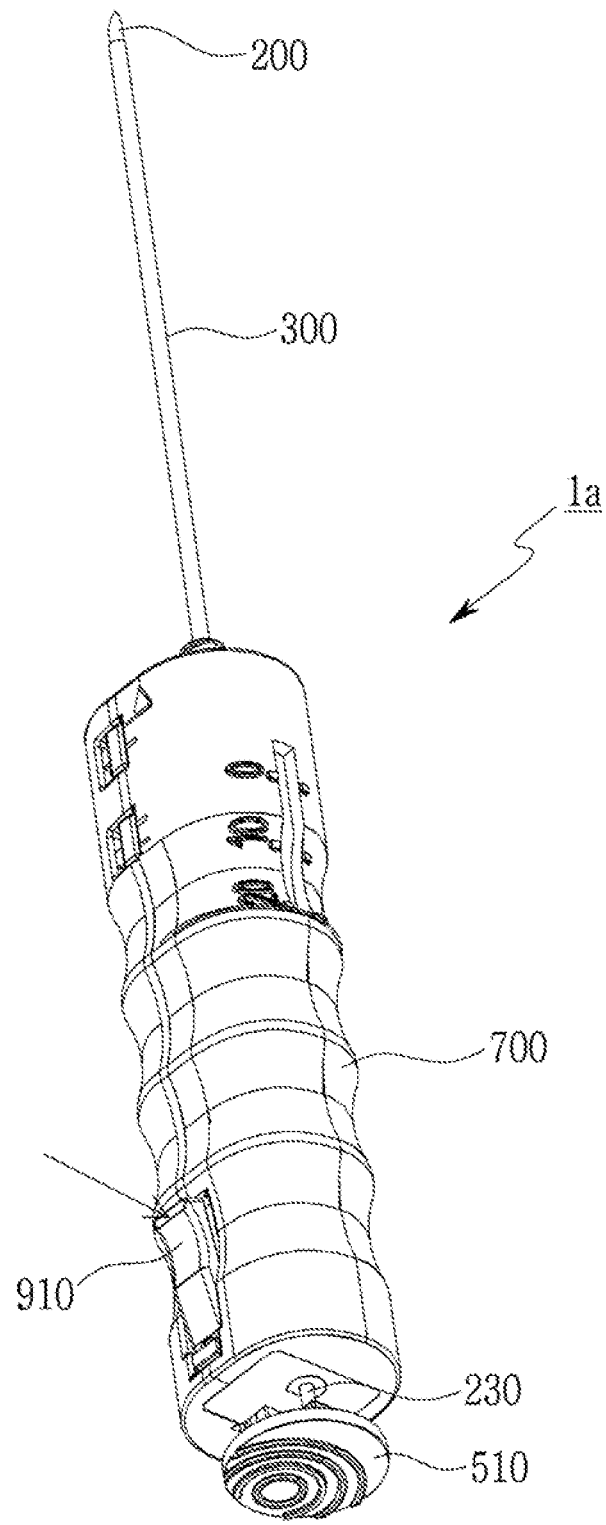

[Fig. 11]
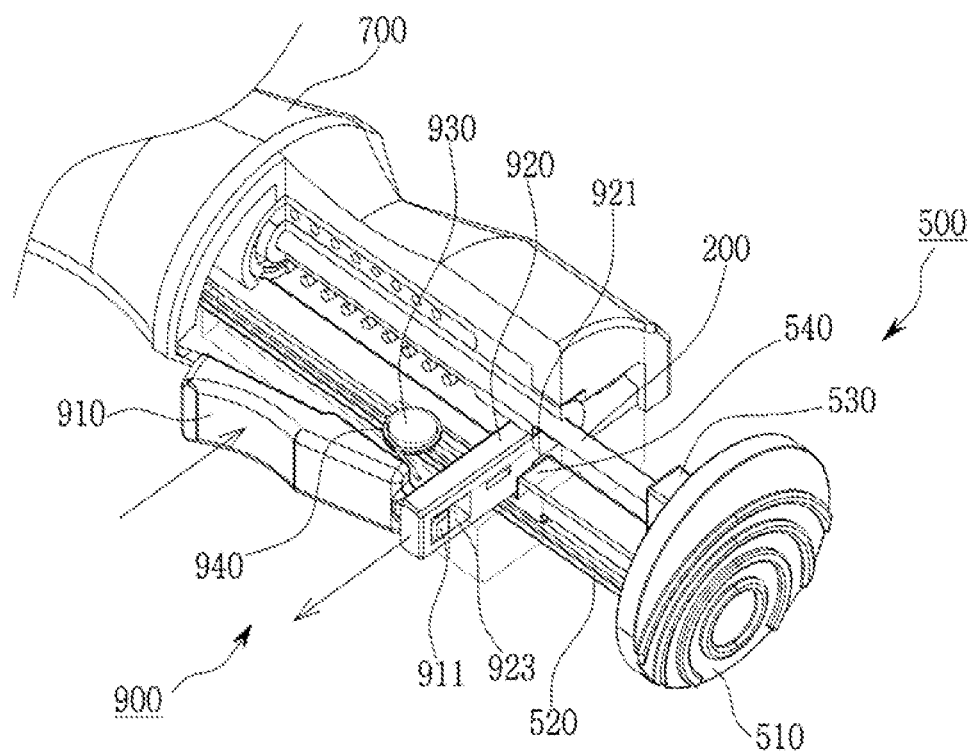

[Fig. 12]
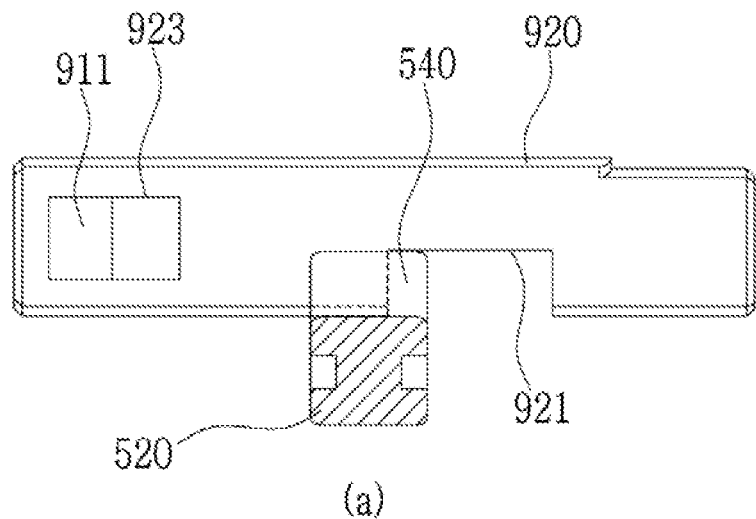
(a)
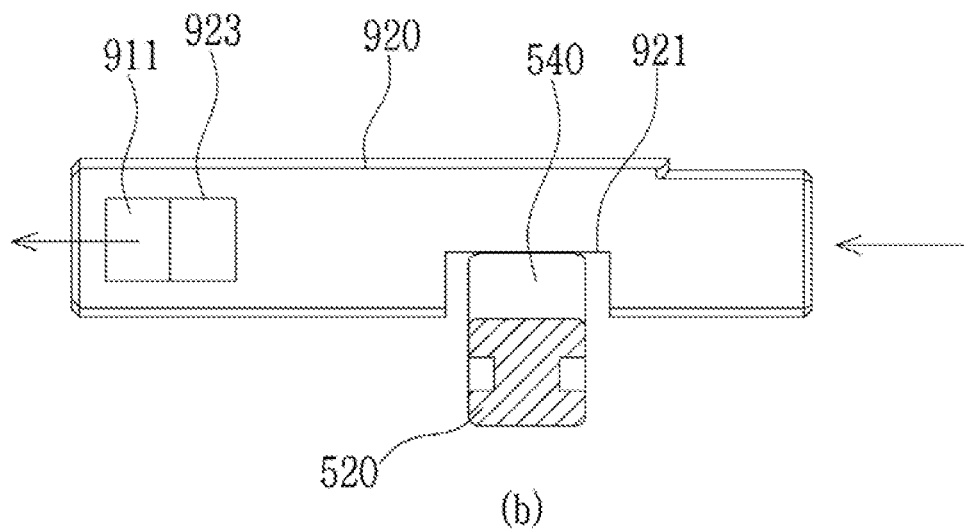
(b)

BIOPSY INSTRUMENT HAVING OUTER NEEDLE-LOCKING MEMBER

CROSS REFERENCE TO RELATED APPLICATIONS

This application is a National Stage of International Application No. PCT/KR2020/019424 filed Dec. 30, 2020, claiming priority based on Korean Patent Application No. 10-2020-0161268 filed Nov. 26, 2020, the entire disclosures of which are incorporated herein by reference.

TECHNICAL FIELD

The present invention relates to a biopsy instrument, and more particularly to a biopsy instrument capable of checking whether an inner needle is placed in target tissue and shooting an outer needle after the tissue is sufficiently introduced into the inner needle, thereby accurately collecting the target tissue that is to be examined.

BACKGROUND ART

In general, for the examination of biological tissue, a method of inserting an instrument for sampling the biological tissue into the biological tissue and collecting a portion of the biological tissue that is to be examined is used.

To this end, cutting biopsy, which acquires tissue by cutting out the same using a needle while keeping the histological configuration thereof intact, and which exhibits high diagnostic accuracy, has recently been used. Cutting biopsy is currently widely used because it enables minimization of the diameter of a needle inserted into an affected part, minimization of repetitive invasive procedures, and a precise medical procedure for a small-sized specimen.

A conventional biopsy instrument disclosed in Korean Patent Registration No. 10-1463867 or No. 10-1551311 includes an inner needle having therein a tissue collection recess and an outer needle formed so as to surround the inner needle and to be movable forwards and having a blade formed at the distal end thereof in order to cut tissue.

The conventional biopsy instrument is used in the manner of first shooting the inner needle forwards, secondarily shooting the outer needle forwards such that a specimen is introduced into the tissue collection recess in the inner needle, and cutting out the specimen using the blade of the outer needle.

However, because the conventional biopsy instrument has no locking device for locking the outer needle when it is intended to shoot the outer needle forwards after shooting the inner needle forwards, there is a problem in that the outer needle may be shot by accident in the state in which a practitioner inserts the inner needle into the wrong area or in that the outer needle may be shot suddenly before a sufficient amount of tissue is introduced into the inner needle.

DISCLOSURE

Technical Problem

The present invention has been made in order to solve the above problems, and it is an object of the present invention to provide a biopsy instrument capable of controlling the timing at which to shoot an outer needle such that the outer needle is shot when an inner needle accurately reaches target tissue.

The above object and various advantages of the present invention will be more clearly understood by those skilled in the art from preferred embodiments of the present invention.

Technical Solution

The object of the present invention can be accomplished by a biopsy instrument having an outer needle-locking member. The biopsy instrument of the present invention includes: a base 100 formed to have a predetermined length; a needle carrier 400 provided so as to be movable forwards and backwards in a longitudinal direction along the upper surface of the base 100; a trigger 500 including a grip button 510 disposed at the rear end of the base 100 and a carrier connection bar 520 extending from the grip button 510 to the needle carrier 400 so as to be detachably coupled to the needle carrier 400; an outer needle 300 coupled to the front end of the needle carrier 400; an inner needle 200 having a rear end coupled to the grip button 510 through the interior of the outer needle 300 and a collection recess 220 formed in the front end thereof to a predetermined depth; an outer needle drive unit 600 provided between the rear end of the base 100 and the needle carrier 400, the outer needle drive unit having a spring 610 to provide driving force so that the outer needle 300 is resiliently shot; a casing 700 covering the upper portion of the base 100, wherein the outer needle 300 and the inner needle 200 are moved to realize a neutral state in which the outer needle 300 surrounds the inner needle 200 so as to be located at the same position as the front end of the inner needle 200, a loaded state in which the needle carrier 400 is moved backwards by the trigger 500 such that the outer needle 300 and the inner needle 200 are moved backwards together from the neutral state and such that the spring 610 is compressed, an inserted state in which the trigger 500 is moved forwards from the loaded state such that only the inner needle 200 is moved forwards into target tissue, and a collecting state in which the outer needle 300 is shot by the spring 610 to cut and collect the target tissue; and a locking member 800 formed perpendicular to the movement route of the carrier connection bar 520, the locking member being configured to open and close the movement route of the carrier connection bar 520 so as to control movement of the outer needle 300 in the inserted state depending on whether an unlocking button 830, protruding to the outside of the casing 700, is pressed.

In one embodiment, the trigger 500 includes: an inner needle-coupling bar 530 protruding from the grip button 510 toward the base 100 so as to be coupled to the inner needle 200; and a locking catching bar 540 formed between the carrier connection bar 520 and the inner needle-coupling bar 530 such that the movement route thereof is closed by the locking member 800. The carrier connection bar 520 includes a traction protrusion 521 formed at the front end thereof so as to protrude upwards. The locking member 800 includes: a lower rotary member 810 formed to have an arc-shaped outer circumference, the lower rotary member having therein a bar movement hole 815 formed corresponding to the sectional shape of a movement position limiting bar 525, the lower rotary member being disposed on the bottom surface of the base 100; an upper pressing member 820 formed to have a semicircular-shaped section, the upper pressing member having one end, fixed to one end of the lower rotary member 810, and a remaining end, spaced apart from the remaining end of the lower rotary member 810 by a predetermined distance; and an unlocking button 830 protruding from the upper surface of the upper pressing member 820 so as to be exposed to the outside of the casing 700. When the unlocking button 830 is not pressed, the bar movement hole 815 is misaligned from the locking catching bar 540 such that the locking catching bar 540 is prevented from being moved forwards, and when the unlocking button 830 is pressed, the upper pressing member 820 is moved downwards to press the lower rotary member 810 such that the lower rotary member 810 is rotated on the surface of the base 100, and the bar movement hole 815 is coaxially aligned with the locking catching bar 540 such that the locking catching bar 540 is allowed to be moved forwards.

According to one embodiment, the needle carrier 400 includes: a carrier body 410 including side fitting wings 411 protruding from both sides thereof and a protrusion-fitting hole 415 formed through the rear end thereof to allow the traction protrusion 521 to be fitted thereinto; and a needle-coupling block 420 protruding upwards from the carrier body 410, the needle-coupling block being coupled at the front portion thereof to the outer needle 300 and coupled at the rear portion thereof to the spring 610, and the base 100 includes: a base plate 110 including carrier movement rails 111 to which the side fitting wings 411 of the needle carrier 400 are movably coupled, a traction protrusion coupling hole 114 formed therein so as to correspond to the protrusion-fitting hole 415, and a connection bar movement path 113 formed from the traction protrusion coupling hole 114 to the rear end thereof to allow the carrier connection bar 520 to be moved along the connection bar movement path; and a curved locking-member guide surface 130 formed at the rear end of the base plate 110 so as to have a predetermined curvature to rotatably support the lower rotary member 810 of the locking member 800.

Advantageous Effects

A biopsy instrument according to the present invention includes a locking member to prevent an outer needle, which is drawn back in a loaded state, from being shot when not intended by the practitioner. Accordingly, when the practitioner operates a trigger in the state of pressing an unlocking button, the outer needle is shot, thereby accurately sampling target tissue.

In addition, since the biopsy instrument is operable with one hand, there is an advantage in that the practitioner is capable of using the biopsy instrument alone while operating the biopsy instrument with one hand and operating an ultrasound device with the other hand.

DESCRIPTION OF DRAWINGS

FIG. 1 is a perspective view showing the external configuration of a biopsy instrument according to the present invention, FIGS. 2 and 3 are exploded perspective views showing the configuration of the biopsy instrument according to the present invention when viewed from different angles, FIG. 4 is a bottom perspective view showing the bottom configuration of the biopsy instrument of the present invention, FIG. 5 is a perspective view showing the internal configuration of the biopsy instrument of the present invention in a neutral state and a loaded state, FIG. 6 is a sectional view showing the operation of a locking member of the biopsy instrument of the present invention, FIG. 7 is a sectional view showing the sectional configuration of the biopsy instrument of the present invention in the neutral state, FIG. 8 is a sectional view showing the sectional configuration of the biopsy instrument of the present invention in the loaded state and an inserted state, FIG. 9 is a sectional view showing the sectional configuration of the biopsy instrument of the present invention in a collecting state.

FIG. 10 is a perspective view showing the configuration of a biopsy instrument according to another embodiment of the present invention, FIG. 11 is a partially-cut perspective view showing the configuration of a side locking unit of the biopsy instrument according to the other embodiment of the present invention, and FIG. 12 is a sectional view showing the operation of the side locking unit of the biopsy instrument according to the other embodiment of the present invention.

BEST MODE

The present invention will now be described more fully with reference to the accompanying drawings, in which preferred embodiments of the invention are shown. The present invention may, however, be embodied in many different forms, and should not be construed as being limited to the embodiments set forth herein. Rather, these embodiments are provided so that this disclosure will be thorough and complete, and will fully convey the scope of the invention to those skilled in the art. In the drawings, the shapes of components may be exaggerated for clarity of explanation. In the drawings, the same elements are denoted by the same reference numerals. In the following description, a detailed description of known functions and configurations incorporated herein will be omitted when it may make the subject matter of the present invention rather unclear.

FIG. 1 is a perspective view showing the external configuration of a biopsy instrument 1 according to the present invention, FIGS. 2 and 3 are exploded perspective views showing the configuration of the biopsy instrument 1, and FIG. 4 is a bottom perspective view showing the bottom configuration of the biopsy instrument 1.

FIG. 5 is a perspective view showing the internal structure of the biopsy instrument 1 according to the present invention in a neutral state and a loaded state, and FIG. 6 is a sectional view showing the vertical-sectional configuration of a locking member 800 in the neutral state and a collecting state.

FIG. 7 is a sectional view showing the sectional configuration of the biopsy instrument 1 in the neutral state, (a) of FIG. 8 is a sectional view showing the sectional configuration in the loaded state, (b) of FIG. 8 is a sectional view showing the sectional configuration in an inserted state, and FIG. 9 is a sectional view showing the sectional configuration in the collecting state.

The biopsy instrument 1 according to the present invention is used in order to accurately collect tissue of a target affected part for the purpose of examination of biological tissue.

As shown in FIGS. 1 to 4, the biopsy instrument 1 according to the present invention includes a base 100, an inner needle 200, which is provided so as to protrude from the front end of the base 100 for insertion into biological tissue, an outer needle 300, which is disposed outside the inner needle 200, a trigger 500, which is provided so as to protrude from the rear end of the base 100 to be gripped by the user's hand and to adjust the positions of the inner needle 200, the outer needle 300 and a needle carrier 400, an outer needle drive unit 600, which is provided between the needle carrier 400 and the rear end of the base 100 in order to enable the outer needle 300 to be shot forwards and to perform a collection process, a casing 700, which covers the upper side of the base 100, and a locking member 800, which is provided at the rear end of the base 100 in order to limit the movement of the outer needle 300.

The biopsy instrument 1 according to the present invention is provided in a neutral state in which the inner needle 200 and the outer needle 300 protrude the same length outside the base 100, as shown in FIG. 7. The practitioner draws the trigger 500 back in the neutral state in order to collect tissue, whereby the neutral state is switched to a loaded state in which the inner needle 200 and the outer needle 300 are drawn back together, as shown in (a) of FIG. 8.

In the loaded state, in which the inner needle 200 and the outer needle 300 are drawn back, as shown in (a) of FIG. 8, the practitioner inserts the inner needle 200 and the outer needle 300 into an area close to the target tissue B that is to be sampled while inspecting biological tissue A using ultrasound.

At this time, the inner needle 200 and the outer needle 300 are placed at a position spaced 7 to 10 mm apart from the target tissue B. Subsequently, as shown in (b) of FIG. 8, the trigger 500 is pressed forwards in order to realize an inserted state in which only the inner needle 200 is inserted into the target tissue B.

When it is determined through ultrasound that the inner needle 200 has accurately reached the target tissue B and that a portion of the target tissue B is introduced into a collection recess 220 in the inner needle 200, the trigger 500 is pressed further forwards, as shown in FIG. 9, in order to realize a collecting state in which the outer needle 300 moves so as to cover a front tip 210 of the inner needle 200. The outer needle 300 is shot at a high speed so as to cover the inner needle 200 by the elastic force of the outer needle drive unit 600, and cuts the tissue, thereby collecting the target tissue B in the collection recess 220.

Here, the biopsy instrument 1 according to the present invention includes the locking member 800 in order to allow the inner needle 200 to move forwards while preventing the outer needle 300 from moving forwards in the inserted state. Accordingly, when the practitioner presses an unlocking button 830 of the locking member 800, which protrudes to the outside of the casing 700, the outer needle 300 is allowed to move forwards, thereby solving the problems with the conventional biopsy instrument in which an outer needle is shot by accident without the practitioner's intention and in which the amount of biological tissue that is collected is not sufficient.

The base 100 supports the inner needle 200, the outer needle 300, and the needle carrier 400 so that these components are moved forwards and backwards by being pressed by the trigger 500. As shown in FIGS. 2 and 3, the base 100 includes a plate-shaped base plate 110 having a predetermined length, side walls 120 formed vertically on the edge of the base plate 110, and a curved locking-member guide surface 130 formed inside the rear end of the base plate 110.

Carrier movement rails 111 for guiding the forward and backward movement of the needle carrier 400, a connection bar movement path 113 for guiding the forward and backward movement of a carrier connection bar 520 of the trigger 500, and a traction protrusion support plate 115 on which a traction protrusion 521 of the carrier connection bar 520 is mounted are formed on the surface of the base plate 110.

The carrier movement rails 111 have predetermined lengths, and are formed on both sides of the base plate 110 such that side fitting wings 411 formed on both sides of the needle carrier 400 are fitted thereinto. The carrier movement rails 111 guide the needle carrier 400, which is located at the front portion of the base plate 110 in the neutral state, as shown in (a) of FIG. 5, to move backwards to the position corresponding to the loaded state, as shown in (b) of FIG. 5. The lengths of the carrier movement rails 111 are set to the distance that the needle carrier 400 moves from the neutral state to the loaded state.

The connection bar movement path 113 guides the carrier connection bar 520 of the trigger 500 to move forwards and backwards so as to draw or press the needle carrier 400 to realize the neutral state, the loaded state, and the collecting state. As shown in FIGS. 2 and 3, the connection bar movement path 113 is formed in a straight line shape from a traction protrusion coupling hole 114 to the rear end of the base plate 110.

Guide protrusions 113a having predetermined lengths are formed on both sides of the connection bar movement path 113 so as to protrude toward the inside of the connection bar movement path 113. The guide protrusions 113a are inserted into side guide grooves 523 formed in both sides of the carrier connection bar 520, and thus support the movement of the carrier connection bar 520 along the connection bar movement path 113.

The traction protrusion support plate 115 supports the lower portion of the traction protrusion 521 so that the traction protrusion 521 of the carrier connection bar 520 is coupled to the needle carrier 400. As shown in an enlarged manner in FIGS. 2, 3 and 7, the traction protrusion support plate 115 supports the lower portion of the traction protrusion 521, which is formed at the front end of the carrier connection bar 520 moving along the connection bar movement path 113, thereby enabling the traction protrusion 521 to catch in the needle carrier 400 coupled to the upper surface of the base plate 110.

The traction protrusion support plate 115 is formed horizontally, and is connected to a traction protrusion loading plate 115b, which is formed to be slanted downwards. The traction protrusion coupling hole 114 is formed through the rear end of the traction protrusion loading plate 115b. As shown in FIG. 4, the traction protrusion 521 moves forwards along the connection bar movement path 113 to the traction protrusion loading plate 115b through the traction protrusion coupling hole 114, and is then inserted into a protrusion-fitting hole 415 in the needle carrier 400 and is caught therein.

Here, as shown in an enlarged manner in FIG. 2, a pair of protrusion stoppers 115a is formed on both sides of the traction protrusion loading plate 115b so as to protrude upwards. Position-fixing protrusions 430 formed at the lower portion of the needle carrier 400 are caught on the pair of protrusion stoppers 115a.

As shown in FIG. 7, in the neutral state, the needle carrier 400 is disposed at the front end of the base plate 110. As shown in (a) of FIG. 8, when the needle carrier 400 is moved backwards to the position corresponding to the loaded state by being pressed by the trigger 500, the position-fixing protrusions 430, which are formed so as to protrude from the lower portion of the needle carrier 400, are caught on the pair of protrusion stoppers 115a, whereby the needle carrier 400 stays at the position to which the same has been moved backwards.

As shown in FIGS. 2 and 3, the side walls 120 are formed vertically on both sides of the base plate 110. A plurality of casing hook holders 121 is formed on the surfaces of the side walls 120. Coupling hooks 740 of the casing 700 are caught in the casing hook holders 121, thereby maintaining engagement of the base 100 and the casing 700.

A front wall 123 is formed at the front end of the base 100, and a rear wall 125 is formed at the rear end of the base 100. The rear wall 125 has therein an inner needle exposure hole 125a, through which the inner needle 200 is exposed to the outside, and a connection bar insertion hole 125b, which is formed so as to communicate with the connection bar movement path 113 so that the carrier connection bar 520 is inserted into the connection bar movement path 113 therethrough.

The curved locking-member guide surface 130 is formed at the rear end portion of the base plate 110 on which the locking member 800 is disposed, and supports rotation of a lower rotary member 810 of the locking member 800. (a) and (b) of FIG. 6 are sectional views illustrating the operation of the locking member 800.

As shown in (a) of FIG. 6, the curved locking-member guide surface 130 has an inner wall surface that is curved so as to match the diameter of the outer circumference of the lower rotary member 810. Accordingly, in the state in which the unlocking button 830 protrudes upwards, the lower rotary member 810 is disposed at an incline on the curved locking-member guide surface 130, and as shown in (b) of FIG. 6, when the unlocking button 830 is pushed down, the lower rotary member 810 is pressed down and is guided to be rotated along the curved shape of the curved locking-member guide surface 130, and a bar movement hole 815 is located coaxially with a locking catching bar 540.

The inner needle 200 is inserted into the biological tissue A in order to collect the target tissue B. As shown in FIG. 7, in the neutral state, the inner needle 200 is accommodated in the outer needle 300, the front tip 210 thereof is exposed to the outside of the outer needle 300, and a trigger-coupling end 230, which is the rear end thereof, is fixed to an inner needle-coupling bar 530 of the trigger 500.

As shown in (b) of FIG. 8, the collection recess 220 is formed to a predetermined depth in the front end of the inner needle 200. In the inserted state, the inner needle 200 is inserted into the target tissue B, and the target tissue B is introduced into the collection recess 220.

The outer needle 300 is disposed so as to surround the outer periphery of the inner needle 200. The outer needle 300 has a blade formed at the front end 310 thereof. In the loaded state shown in (b) of FIG. 8, in which the outer needle 300 is moved further backwards than the inner needle 200, the outer needle 300 is resiliently shot by the outer needle drive unit 600 to realize the collecting state shown in FIG. 9, thereby cutting the biological tissue surrounding the collection recess 220 so that the target tissue B is collected in the collection recess 220.

As shown in FIG. 2, the rear end 320 of the outer needle 300 is fixed in position in the manner of being fitted into an outer needle-fixing hole 421 in a needle-coupling block 420 of the needle carrier 400. The outer needle 300 is moved forwards and backwards in the manner of being interlocked with the forward and backward movement of the needle carrier 400.

The needle carrier 400 is coupled to the trigger 500, so the outer needle 300 is moved forwards and backwards along the base 100 by the practitioner pressing the trigger 500, whereby the neutral state is switched to the loaded state, the inserted state, and the collecting state.

As shown in FIGS. 2 and 3, the needle carrier 400 includes a carrier body 410 formed corresponding to the width of the base plate 110, a needle-coupling block 420 protruding upwards from the carrier body 410 so as to be coupled to the outer needle 300 and the outer needle drive unit 600, and position-fixing protrusions 430 formed so as to protrude from the lower portion of the carrier body 410 in order to fix the position of the needle carrier 400.

The carrier body 410 is moved forwards and backwards along the base plate 110. The carrier body 410 has side fitting wings 411 formed on both sides thereof so as to be fitted into the carrier movement rails 111 of the base plate 110 to thus support the carrier body 410 to move along the carrier movement rails 111.

As shown in FIG. 3, a protrusion movement guide surface 413 is formed inside the carrier body 410 so as to protrude upwards to a predetermined height, and a protrusion-fitting hole 415, into which the traction protrusion 521 is fitted, is formed behind the protrusion movement guide surface 413.

As shown in an enlarged manner in FIG. 7, in the neutral state, the traction protrusion 521 of the carrier connection bar 520 of the trigger 500 is inserted into the traction protrusion coupling hole 114 in the base plate 110 and is mounted on the traction protrusion loading plate 115b. Then, the traction protrusion 521 is caught in the protrusion-fitting hole 415 in the needle carrier 400. Since a portion of the traction protrusion 521 is formed so as to be oriented in the backward direction, the traction protrusion 521 is caught in the traction protrusion coupling hole 114.

Accordingly, when the user presses the trigger 500 backwards, since the traction protrusion 521 is caught in the protrusion-fitting hole 415, the needle carrier 400 is moved backwards together with the trigger 500 to the position corresponding to the loaded state, as shown in (a) of FIG. 8.

On the other hand, as shown in (b) of FIG. 8, in the inserted state, the needle carrier 400 is maintained in the state of being moved backwards, and only the carrier connection bar 520 is moved forwards. At this time, the traction protrusion 521 is moved forwards along the protrusion movement guide surface 413 in the state in which the upper end thereof is in contact with the protrusion movement guide surface 413, and comes into contact with the traction protrusion support plate 115, thereby realizing the neutral state.

The needle-coupling block 420 protrudes upwards from the carrier body 410. As shown in FIG. 2, the needle-coupling block 420 has an outer needle-fixing hole 421 formed in the front portion thereof to allow the outer needle 300 to be coupled thereto and a spring-coupling protrusion 423 formed at the rear portion thereof to allow a spring 610 of the outer needle drive unit 600 to be coupled thereto.

Accordingly, as shown in (a) of FIG. 5, in the neutral state, when the needle carrier 400 is located at the front portion of the base plate 110, the spring 610 is expanded to the initial length W1 thereof, and as shown in (b) of FIG. 5, in the loaded state, when the needle carrier 400 is moved backwards, the spring 610 is compressed to a second length W2 between the rear wall 125 of the base plate 110 and the needle-coupling block 420.

As shown in FIG. 3, a plurality of position-fixing protrusions 430 is formed so as to protrude from the lower portion of the carrier body 410. As shown in (b) of FIG. 8, when the needle carrier 400 is moved backwards to the position corresponding to the loaded state, the position-fixing protrusions 430 enable the needle carrier 400 to be maintained in the state of being moved backwards.

When the needle carrier 400 is moved backwards by the trigger 500, the position-fixing protrusions 430 are caught on the protrusion stoppers 115a of the traction protrusion support plate 115, whereby the position of the carrier body 410 is fixed.

On the other hand, as shown in an enlarged manner in FIG. 9, when the practitioner presses the carrier connection bar 520 forwards in order to switch the loaded state to the collecting state, the traction protrusion 521 is moved and presses the traction protrusion loading plate 115b downwards, and thus the position-fixing protrusions 430 are separated from the protrusion stoppers 115a. When the position-fixing protrusions 430 are separated from the protrusion stoppers 115a, the needle carrier 400 is moved to the position corresponding to the collecting state by the elastic force of the spring 610.

The practitioner presses the trigger 500 forwards and backwards with the hand in order to adjust the positions of the outer needle 300 and the inner needle 200 such that the needles collect the target tissue while moving to the positions corresponding to the neutral state, the loaded state, the inserted state, and the collecting state.

The trigger 500 includes a grip button 510, which is formed to have a predetermined area in a direction perpendicular to the base 100, a carrier connection bar 520, which extends from the grip button 510 so as to be connected to the needle carrier 400, an inner needle-coupling bar 530, which is formed on the carrier connection bar 520 so as to be coupled to the inner needle 200, and a locking catching bar 540, which is formed between the inner needle-coupling bar 530 and the carrier connection bar 520 such that the movement thereof is controlled by the locking member 800.

As shown in FIG. 1, the grip button 510 is provided behind the casing 700 so that the practitioner is capable of holding the grip button 510 with the hand and pulling or pushing the carrier connection bar 520 backwards or forwards.

The inner needle-coupling bar 530 connects the inner needle 200 to the grip button 510. The trigger-coupling end 230 of the inner needle 200 is fixed to the inner needle-coupling bar 530.

The carrier connection bar 520 is moved along the connection bar movement path 113 of the base plate 110, and is detachably coupled to the needle carrier 400 to move the needle carrier 400 forwards and backwards. The traction protrusion 521 is formed at the front end of the carrier connection bar 520 so as to protrude upwards, and the side guide grooves 523 are formed in both side surfaces of the carrier connection bar 520 in the longitudinal direction. In addition, the carrier connection bar 520 is provided with a movement position limiting bar 525 at a position adjacent to the traction protrusion 521.

As shown in FIG. 7, in the neutral state, the traction protrusion 521 is inserted into the region on the base plate 110 through the traction protrusion coupling hole 114, and is caught in the protrusion-fitting hole 415 in the needle carrier 400. As shown in (a) of FIG. 8, when the practitioner pulls the grip button 510 backwards, the carrier connection bar 520 is moved backwards along the connection bar movement path 113, and the needle carrier 400 caught by the traction protrusion 521 is also moved backwards along the carrier movement rails 111 by the pulling force of the carrier connection bar 520.

As shown in (b) of FIG. 8, when the grip button 510 is pressed forwards in order to realize the inserted state, the traction protrusion 521 is separated from the protrusion-fitting hole 415 in the needle carrier 400 that has been moved backwards, and is moved forwards. Then, in the inserted state, the traction protrusion 521 is located on the traction protrusion loading plate 115b.

The locking catching bar 540 extends from the grip button 510 to a length that enables contact with the rear end of the locking member 800 in the inserted state, as shown in (b) of FIG. 8. In the inserted state, the locking catching bar 540 is caught on the locking member 800 that closes the route of the locking catching bar 540, and is not moved further, and the carrier connection bar 520 is moved until the traction protrusion 521 comes into contact with the traction protrusion loading plate 115b.

As shown in FIG. 9, in the collecting state, the locking member 800 opens the route so that the locking catching bar 540 is capable of moving, and the carrier connection bar 520 is moved so that the traction protrusion 521 presses the traction protrusion loading plate 115b. Accordingly, the traction protrusion loading plate 115b is pressed downwards by the pressure generated by the forward movement of the traction protrusion 521, and the position-fixing protrusions 430 of the needle carrier 400 are separated from the protrusion stoppers 115a, and are shot forwards together with the outer needle 300 by the elastic force of the spring 610.

The outer needle drive unit 600 enables the needle carrier 400 that has been moved backwards to the position corresponding to the loaded state to be shot at a high speed, and enables the outer needle 300 coupled to the needle carrier 400 to move while surrounding the inner needle 200 and to cut the tissue.

The outer needle drive unit 600 includes a spring 610, disposed between the needle carrier 400 and the rear wall 125 of the base 100, and a spring cover 620, covering the upper portion of the spring 610. As shown in (a) of FIG. 5, in the neutral state, the length of the spring 610 is maintained at a first length f1, and as shown in (b) of FIG. 5, in the loaded state, the spring 610 is compressed to a second length f2 by the needle carrier 400 that is moved backwards.

When the locking member 800 releases the locking catching bar 540 and thus the position-fixing protrusions 430 of the needle carrier 400 are separated from the protrusion stoppers 115a, the spring 610 provides the elastic force thereof, by which the spring 610 is restored to the initial length thereof, to the needle carrier 400 so that the needle carrier 400 is rapidly moved forwards to the position corresponding to the neutral state.

Accordingly, the outer needle 300 coupled to the needle carrier 400 is shot into the tissue, and cuts the target tissue.

The spring cover 620 covers the upper portion of the rear end of the spring 610 so that the locking member 800 is capable of operating without interfering with the spring 610. An inner needle guide pipe 621 for guiding the inner needle 200 to the rear wall 125 is formed inside the spring cover 620 in the longitudinal direction. A wall-coupling shaft 623 is formed at the rear end of the spring cover 620 so as to be coupled to the rear wall 125.

The casing 700 covers the upper portion of the base 100 in order to prevent internal components other than the inner needle 200 and the outer needle 300 from being exposed to the outside. The casing 700 is formed to have a size corresponding to that of the base 100. A needle guide pipe 710 is formed at the front portion of the casing 700 in order to expose the outer needle 300 to the outside.

A locking button exposure hole 720 is formed through the upper rear portion of the casing 700 in order to expose the unlocking button 830 of the locking member 800 to the outside, and as shown in FIG. 4, a block movement rail 730 is formed on the upper inner surface of the casing 700 in the longitudinal direction. The block movement rail 730 is formed corresponding to the needle-coupling block 420 of the needle carrier 400 in order to guide the needle carrier 400 to move stably in the forward-backward direction.

The casing 700 has a plurality of coupling hooks 740 formed at both sides of the front lower portion thereof. The coupling hooks 740 are hooked in the casing hook holders 121 of the base 100, so the casing 700 and the base 100 are fixed to each other.

The locking member 800 closes the route of the locking catching bar 540 of the trigger 500 to limit the movement of the locking catching bar 540. Accordingly, the carrier connection bar 520 is prevented from being moved further from the position corresponding to the inserted state, and thus the outer needle 300 is prevented from being shot without the practitioner's intention.

As shown in FIG. 2, the locking member 800 includes a lower rotary member 810 and an upper pressing member 820, which are vertically coupled to each other in the form of handcuffs, and an unlocking button 830, which is formed so as to protrude upwards from the upper pressing member 820.

The upper pressing member 820 is formed in a semicircular shape, and is disposed on the spring cover 620 at a position corresponding to the locking button exposure hole 720 in the casing 700. A pair of support legs 825 extends downwards from both sides of the upper pressing member 820, and is disposed in a direction perpendicular to the base plate 110. Since the pair of support legs 825 is disposed perpendicular to the curved locking-member guide surface 130, the upper pressing member 820 may be disposed above the spring cover 620 so as to be spaced apart therefrom.

The lower rotary member 810 is formed in a semicircular shape such that the outer circumferential surface thereof has a curvature corresponding to that of the curved locking-member guide surface 130. The lower rotary member 810 has one end, at which a coupling end 811 is formed so as to be fixed to the upper pressing member 820, and the other end, which is not fixed. A bar movement hole 815 is formed in the lower surface of the lower rotary member 810 by cutting out a portion of the lower surface.

The unlocking button 830 is formed so as to protrude to the outside of the casing 700 through the locking button exposure hole 720 in the casing 700. When the practitioner presses the unlocking button 830, the position of the lower rotary member 810 is adjusted such that the locking catching bar 540 is unlocked, and at the same time the position-fixing protrusions 430 of the needle carrier 400 are released from the protrusion stoppers 115a.

As shown in (a) of FIG. 6, before the practitioner presses the unlocking button 830, the lower rotary member 810 is disposed so as to be inclined at a predetermined angle on the curved locking-member guide surface 130.

Here, although not shown in the drawings, an elastic support member (not shown) is provided at the coupling end 811 of the lower rotary member 810 and the fixing end 821 of the upper pressing member 820. When the upper pressing member 820 does not press the lower rotary member 810, the elastic support member (not shown) applies elastic force to the fixing end 821 so that the fixing end 821 is located at an elevated position.

Before the unlocking button 830 is pressed, the bar movement hole 815 in the lower rotary member 810 is misaligned from the locking catching bar 540, and thus the movement route of the locking catching bar 540 is closed. That is, as shown in (b) of FIG. 8, the lower rotary member 810 blocks the locking catching bar 540, and thus the locking catching bar 540 and the carrier connection bar 520 are prevented from being moved further forwards.

As shown in (b) of FIG. 6, when the practitioner presses the unlocking button 830 downwards, the upper pressing member 820 presses the lower rotary member 810, and the lower rotary member 810 is rotated along the curved locking-member guide surface 130 such that the bar movement hole 815 is coaxially aligned with the locking catching bar 540.

When the practitioner presses the grip button 510 forwards in the state of pressing the unlocking button 830, the locking catching bar 540 is moved forwards while passing through the lower rotary member 810. Accordingly, as shown in FIG. 9, the carrier connection bar 520 is moved further forwards, and the traction protrusion 521 presses the traction protrusion loading plate 115b downwards, whereby the position-fixing protrusions 430 of the needle carrier 400 are separated from the protrusion stoppers 115a.

As a result, the needle carrier 400 is moved forwards by the elastic force of the spring 610, and the outer needle 300 is shot, thereby cutting the target tissue.

A process of collecting biological tissue using the biopsy instrument 1 according to the present invention having the configuration described above will be described with reference to FIGS. 1 to 9.

As shown in FIG. 1, the biopsy instrument 1 according to the present invention is packaged and provided in the neutral state. The biopsy instrument 1 is discarded after a single use.

The practitioner holds the casing 700 of the biopsy instrument 1 with one hand, holds the grip button 510 with the other hand, and pulls the grip button 510 backwards in order to move the inner needle 200 and the outer needle 300 to the position corresponding to the loaded state. As shown in FIG. 7, in the neutral state, the inner needle 200 and the outer needle 300 are disposed such that the front ends thereof overlap each other.

As shown in (a) of FIG. 8, when the practitioner pulls the grip button 510 backwards, the traction protrusion 521 of the carrier connection bar 520 is caught in the protrusion-fitting hole 415, and thus the needle carrier 400 is moved backwards. At this time, the spring 610 is compressed by the backward movement of the needle carrier 400. The position-fixing protrusions 430 are caught on the protrusion stoppers 115a, whereby the needle carrier 400 stays at the position to which the same has been moved backwards on the base plate 110. Accordingly, the inner needle 200 and the outer needle 300 are moved backwards together.

In the loaded state, the practitioner inserts both the inner needle 200 and the outer needle 300 into the biological tissue A while inspecting the same using ultrasound. At this time, the outer needle 300 and the inner needle 200 are placed at a position spaced apart from the target tissue B by a predetermined distance.

Subsequently, as shown in (b) of FIG. 8, the practitioner presses the grip button 510 forwards in order to insert only the inner needle 200 into the target tissue B. When the grip button 510 is pressed, the traction protrusion 521 of the carrier connection bar 520 is moved forwards along the protrusion movement guide surface 413 of the needle carrier 400 to be brought into contact with the traction protrusion loading plate 115b in the state in which the locking catching bar 540 contacts the locking member 800.

The practitioner checks whether the inner needle 200 is accurately inserted into the target tissue using ultrasound, and allows the target tissue to be sufficiently introduced into the collection recess 220 in the inner needle 200 for a predetermined time period.

Subsequently, as shown in (b) of FIG. 6, when the unlocking button 830 is pressed, the upper pressing member 820 presses the lower rotary member 810, and the lower rotary member 810 is rotated such that the bar movement hole 815 is coaxially aligned with the locking catching bar 540.

When the practitioner presses the grip button 510 forwards in the state of pressing the unlocking button 830, the unlocking button 830 is inserted into the bar movement hole 815, and the traction protrusion 521 of the carrier connection bar 520 is moved forwards to press the traction protrusion loading plate 115b downwards. Thereby, the position-fixing protrusions 430 of the needle carrier 400 are separated from the protrusion stoppers 115a.

At the same time, the spring 610 that has been compressed is elastically restored to the initial length, the needle carrier 400 is moved to the front portion of the base 100, and the outer needle 300 coupled to the needle carrier 400 is shot so as to surround the front end of the inner needle 200. In this process, the front end of the outer needle 300 cuts the target tissue surrounding the collection recess 220 to collect the target tissue B.

The practitioner removes the biopsy instrument 1, which is in the neutral state after the completion of the collection, from the patient's body. Subsequently, a sterile container is prepared, and the grip button 510 is pulled backwards to the position corresponding to the loaded state, and is then pushed forwards to the position corresponding to the inserted state in order to expose the inner needle 200 to the outside of the outer needle 300, thereby making it possible to separate the target tissue B from the collection recess 220.

Meanwhile, FIGS. 10 to 12 are views showing the configuration of a biopsy instrument 1a according to another embodiment of the present invention.

In the biopsy instrument 1 of the preferred embodiment described above, the unlocking button 830 is disposed on the upper surface of the casing 700. In contrast, the biopsy instrument 1a of another embodiment includes a side locking unit 900, which has a side unlocking button 910 provided on the side surface of the casing 700.

As shown in FIG. 11, the side locking unit 900 includes a side unlocking button 910, which is pressed by the practitioner, a locking bar 920, which is moved leftwards and rightwards depending on whether the side unlocking button 910 is pressed, a torsion spring 940, which resiliently supports the side unlocking button 910, and an elastic member support shaft 930, to which the torsion spring 940 is coupled.

The side unlocking button 910 is provided on the surface of the casing 700 so as to be moveable leftwards and rightwards by the torsion spring 940. A bar-coupling shaft 911, which is provided at one end of the side unlocking button 910, is coupled to the locking bar 920, and when the practitioner presses the side unlocking button 910, the locking bar 920 is moved in the opposite direction.

The locking bar 920 has a bar movement path 921 formed therein, and when the side unlocking button 910 is not pressed, as shown in (a) of FIG. 12, the bar movement path 921 is misaligned from the locking catching bar 540, thereby preventing the movement of the locking catching bar 540.

On the other hand, when the side unlocking button 910 is pressed, as shown in (b) of FIG. 12, the locking bar 920 is moved linearly, and the bar movement path 921 is coaxially aligned with the locking catching bar 540, thereby allowing the movement of the locking catching bar 540.

As described above, the biopsy instrument according to the present invention includes the locking member to prevent the outer needle, which is drawn back in the loaded state, from being shot when not intended by the practitioner. Accordingly, when the practitioner operates the trigger in the state of pressing the unlocking button, the outer needle is shot, thereby accurately sampling target tissue.

The embodiments of the biopsy instrument of the present invention as described above is only illustrative, and it will be understood by those skilled in the art that various modifications and other equivalent exemplary embodiments may be made. Therefore, it will be understood that the present invention is not limited only to the forms mentioned in the detailed description. Accordingly, the true technical scope of the present invention should be defined by the technical spirit of the appended claims. In addition, it is to be understood that the present invention includes all modifications, equivalents, and substitutions that fall within the spirit and scope of the present invention as defined by the appended claims.

DESCRIPTION OF REFERENCE NUMERALS

1: biopsy instrument 100: base
110: base plate 111: carrier movement rail
113: connection bar movement path 113a: guide protrusion
114: traction protrusion coupling hole 115: traction protrusion support plate
115a: protrusion stopper 115b: traction protrusion loading plate
120: side wall 121: casing hook holder
123: front wall 125: rear wall
125a: inner needle exposure hole 125b: connection bar insertion hole
130: curved locking-member guide surface 200: inner needle
210: front tip 220: collection recess
230: trigger-coupling end 300: outer needle
310: front end 320: rear end
400: needle carrier 410: carrier body
411: side fitting wing 413: protrusion movement guide surface
415: protrusion-fitting hole 420: needle-coupling block
421: outer needle-fixing hole 423: spring-coupling protrusion
430: position-fixing protrusion 500: trigger
510: grip button 520: carrier connection bar
521: traction protrusion 523: side guide groove
525: movement position limiting bar 530: inner needle-coupling bar
540: locking catching bar 600: outer needle drive unit
610: spring 620: spring cover
621: inner needle guide pipe 623: wall-coupling shaft
700: casing 710: needle guide pipe
720: locking button exposure hole 730: block movement rail
740: coupling hook 800: locking member
810: lower rotary member 811: coupling end
813: contact protrusion 815: bar movement hole
820: upper pressing member 821: fixing end
825: support leg 830: unlocking button
900: side locking unit 910: side unlocking button 911: bar-coupling shaft 920: locking bar
921: bar movement path 923: shaft-coupling hole
930: elastic member support shaft 940: torsion spring
A: biological tissue
B: target tissue

INDUSTRIAL APPLICABILITY

The biopsy instrument according to the present invention is configured to prevent an outer needle, which is drawn back in a loaded state, from being shot when not intended by the practitioner, and is advantageous in that it is easy to use because it is operable with one hand.

The invention claimed is:

1. A biopsy instrument comprising:
a base (100) formed to have a predetermined length;
a needle carrier (400) provided so as to be movable forwards and backwards in a longitudinal direction along an upper surface of the base (100);
a trigger (500) comprising a grip button (510) disposed at a rear end of the base (100) and a carrier connection bar (520) extending from the grip button (510) to the needle carrier (400) and detachably coupled to the needle carrier (400);
an outer needle (300) coupled to a front end of the needle carrier (400);
an inner needle (200) having a rear end coupled to the grip button (510) through an interior of the outer needle (300) and a collection recess (220) formed in a front end thereof to a predetermined depth;
an outer needle drive unit (600) provided between a rear end of the base (100) and the needle carrier (400), the outer needle drive unit having a spring (610) to provide a driving force so that the outer needle (300) is resiliently shot;
a casing (700) covering an upper portion of the base (100),
wherein the outer needle (300) and the inner needle (200) are configured to be moved to realize
a neutral state in which the outer needle (300) surrounds the inner needle (200) so as to be located at a same position as the front end of the inner needle (200), a loaded state in which the needle carrier (400) is moved backwards by the trigger (500) such that the outer needle (300) and the inner needle (200) are moved backwards together from the neutral state and such that the spring (610) is compressed, an inserted state in which the trigger (500) is moved forwards from the loaded state such that only the inner needle (200) is moved forwards into target tissue, and a collecting state in which the outer needle (300) is shot by the spring (610) to cut and collect the target tissue; and
a locking member (800) formed perpendicular to a movement route of the carrier connection bar (520), the locking member being configured to open and close the movement route of the carrier connection bar (520) so as to control movement of the outer needle (300) in the inserted state depending on whether an unlocking button (830), protruding to an outside of the casing (700), is pressed.

2. The biopsy instrument according to claim 1, wherein the trigger (500) comprises:
an inner needle-coupling bar (530) protruding from the grip button (510) toward the base (100) so as to be coupled to the inner needle (200); and
a locking catching bar (540) formed between the carrier connection bar (520) and the inner needle-coupling bar (530) such that a movement route thereof is closed by the locking member (800),
wherein the carrier connection bar (520) comprises a traction protrusion (521) formed at a front end thereof so as to protrude upwards,
wherein the locking member (800) comprises:
a lower rotary member (810) formed to have an arc-shaped outer circumference, the lower rotary member having therein a bar movement hole (815) formed corresponding to a sectional shape of a movement position limiting bar (525), the lower rotary member being disposed on a bottom surface of the base (100);
an upper pressing member (820) formed to have a semi-circular-shaped section, the upper pressing member comprising one end, fixed to one end of the lower rotary member (810), and a remaining end, spaced apart from a remaining end of the lower rotary member (810) by a predetermined distance; and
the unlocking button (830) protruding from an upper surface of the upper pressing member (820) so as to be exposed to an outside of the casing (700),
wherein, when the unlocking button (830) is not pressed, the bar movement hole (815) is misaligned from the locking catching bar (540) such that the locking catching bar (540) is prevented from being moved forwards, and
wherein, when the unlocking button (830) is pressed, the upper pressing member (820) is moved downwards to press the lower rotary member (810) such that the lower rotary member (810) is rotated on a surface of the base (100), and the bar movement hole (815) is coaxially aligned with the locking catching bar (540) such that the locking catching bar (540) is allowed to be moved forwards.

3. The biopsy instrument according to claim 2, wherein the needle carrier (400) comprises:
a carrier body (410) comprising side fitting wings (411) protruding from both sides thereof and a protrusion-fitting hole (415) formed through a rear end thereof to allow the traction protrusion (521) to be fitted thereinto; and
a needle-coupling block (420) protruding upwards from the carrier body (410), the needle-coupling block being coupled at a front portion thereof to the outer needle (300) and coupled at a rear portion thereof to the spring (610), and
wherein the base (100) comprises:
a base plate (110) comprising carrier movement rails (111) to which the side fitting wings (411) of the needle carrier (400) are movably coupled, a traction protrusion coupling hole (114) formed therein so as to correspond to the protrusion-fitting hole (415), and a connection bar movement path (113) formed from the traction protrusion coupling hole (114) to a rear end thereof to allow the carrier connection bar (520) to be moved along the connection bar movement path; and
a curved locking-member guide surface (130) formed at the rear end of the base plate (110) so as to have a predetermined curvature to rotatably support the lower rotary member (810) of the locking member (800).

* * * * *